United States Patent [19]

Johnston et al.

[11] 4,027,669

[45] June 7, 1977

[54] DESTRUCTIBLE LUER LOCK SYRINGE AND METHOD OF DESTRUCTING SAME

[75] Inventors: Donald Leroy Johnston, Arcadia; Manuel Garfield Perkins, Gardena; Lynn Zaugg Youngberg, Long Beach, all of Calif.

[73] Assignee: American Hospital Supply Corporation, Evanston, Ill.

[22] Filed: Apr. 12, 1976

[21] Appl. No.: 676,232

[52] U.S. Cl. .............................. 128/218 N; 128/221
[51] Int. Cl.² ................................... A61M 5/00
[58] Field of Search .... 128/218 N, 218 NV, 218 R, 128/221, 247, 215, 216

[56] References Cited

UNITED STATES PATENTS

| | | | |
|---|---|---|---|
| 3,301,256 | 1/1967 | Cowley | 128/218 N |
| 3,320,954 | 5/1967 | Cowley | 128/218 N |
| 3,469,581 | 9/1969 | Burke | 128/218 N X |
| 3,712,302 | 1/1973 | Burke et al. | 128/218 N |
| 3,727,613 | 4/1973 | Sorenson et al. | 128/221 |
| 3,774,606 | 11/1973 | Norton | 128/221 |
| 3,974,832 | 8/1976 | Kruck | 128/221 |

*Primary Examiner*—John D. Yasko
*Attorney, Agent, or Firm*—Larry N. Barger

[57] ABSTRACT

A destructible hypodermic syringe with a segmented Luer lock sleeve surrounding a scored needle adapter. The individual segments of this sleeve have sufficient lateral stability to lock a needle on the adapter, and at least one segment can flex laterally in an outward direction so the adapter can be broken at its scored line.

18 Claims, 6 Drawing Figures

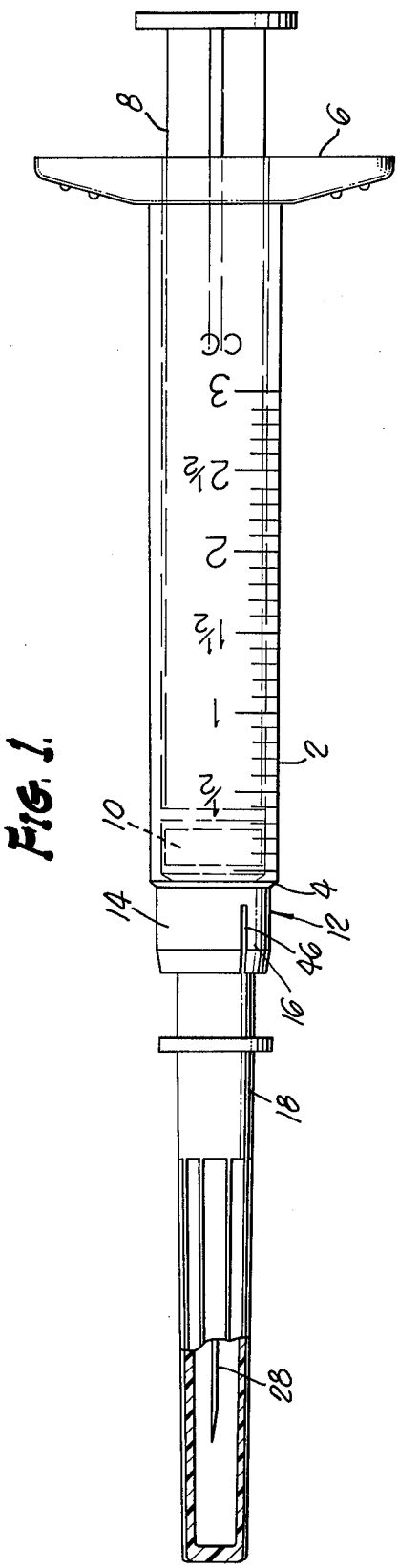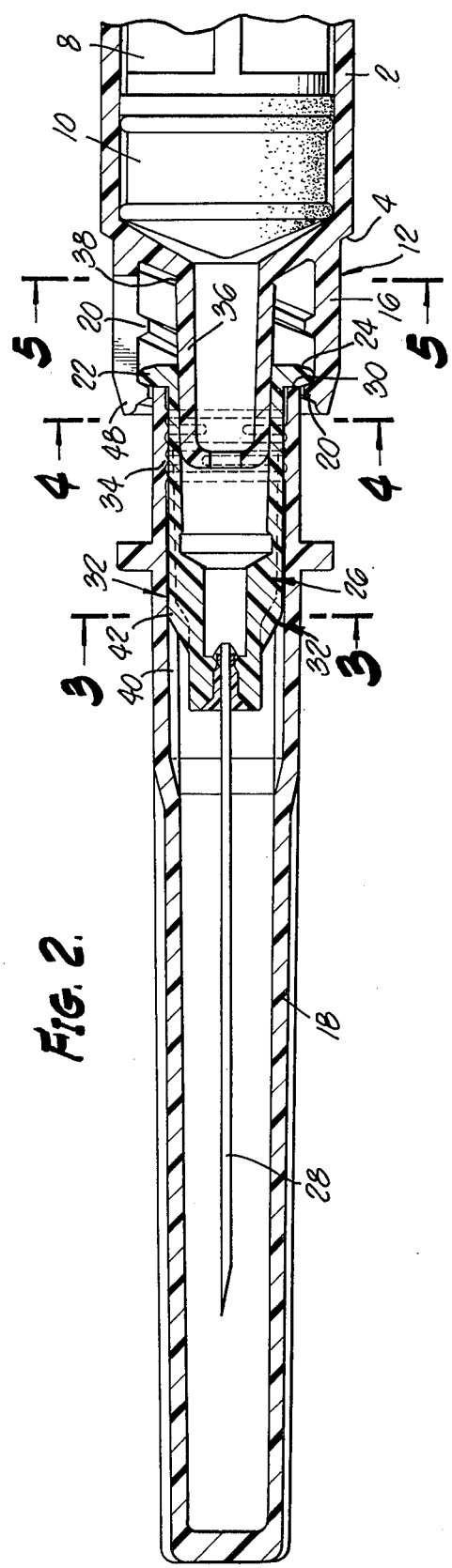

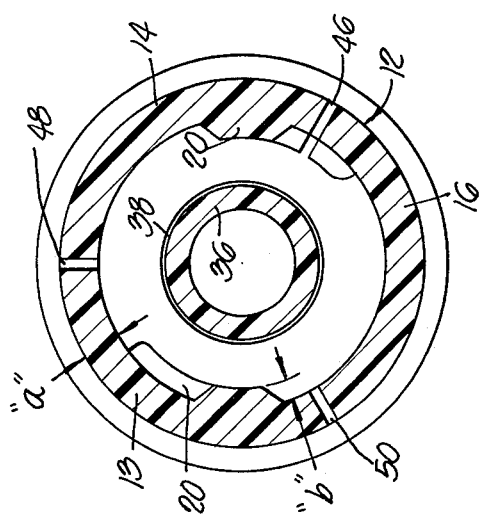
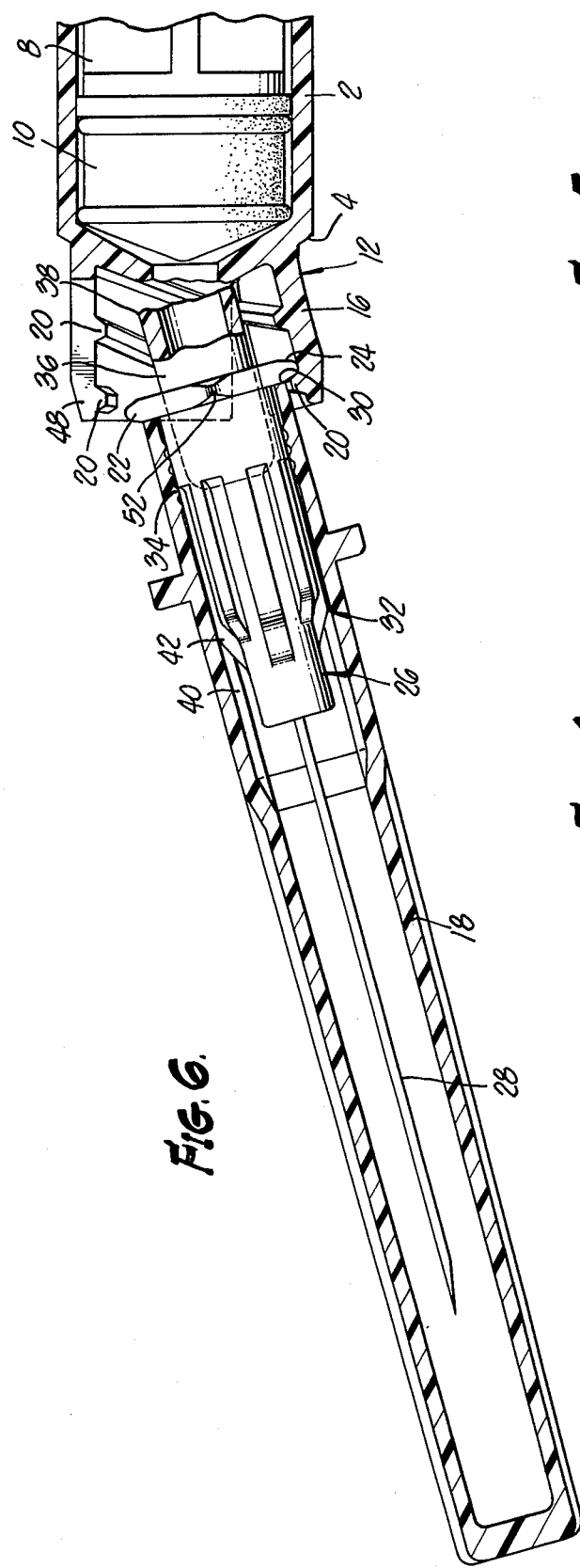
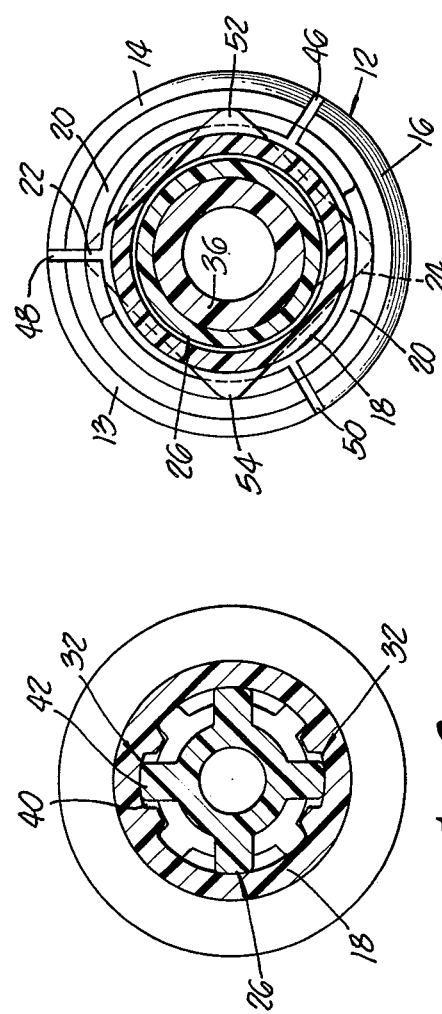

DESTRUCTIBLE LUER LOCK SYRINGE AND METHOD OF DESTRUCTING SAME

BACKGROUND

After a hypodermic syringe has been used by a physician or nurse to give an injection to a patient, it is recommended that this syringe be altered to prevent reuse. The Cowley U.S. Pat. No. 3,320,954 describes one system of altering the syringe. This includes breaking the needle adapter at a circumferential score line.

In the past such a scored needle adapter system for altering the syringe was not suitable for syringes hving a Luer lock sleeve. The rigid Luer lock sleeve surrounding the needle adapter prevented bending the needle adapter to its breaking point. The relationship between the Luer lock sleeve and the needle adapter is shown in the Cowley U.S. Pat. No. 3,301,256. In this Cowley patent a rigid band on a segmented Luer lock sleeve prevented any significant outward flexure of the Luer lock sleeve.

SUMMARY OF THE INVENTION

Applicants' invention relates to the combination of a scored needle adapter and a laterally flexible lug that extends from a forward end of a syringe barrel beyond the needle adapter score. This lug has sufficient lateral stability to lock the hypodermic needle to the needle adapter. Unexpectedly, this laterally flexible lug does not loosen its grip on the needle hub until intentionally bent outwardly by manual force applied by a nurse or physician. In a method of destruction, the needle adapter is bent toward said flexible lug causing it to laterally flex outwardly a sufficient distance to permit breaking the needle adapter at the score line.

In a preferred embodiment, a series of these outwardly flexible lugs surround a scored adapter forming a segmented Luer lock collar.

THE DRAWINGS

FIG. 1 is a side elevational view of the syringe with attached needle and needle protector;

FIG. 2 is an enlarged sectional view of the Luer lock and needle adapter section of the syringe shown in FIG. 1;

FIG. 3 is an enlarged sectional view taken along line 3—3 of FIG. 2;

FIG. 4 is an enlarged sectional view taken along line 4—4 of FIG. 2;

FIG. 5 is an enlarged sectional view taken along line 5—5 of FIG. 2; and

FIG. 6 is a sectional side elevational view of the syringe as its adapter is being fractured.

DETAILED DESCRIPTION

Referring to these drawings a hypodermic syringe barrel 2 is shown having a forward end 4 and a rearward end 6. A conventional syringe plunger 8 with attached resilient stopper 10 longitudinally slides through syringe barrel 2.

Integrally formed with a forward end 4 of the syringe barrel is a Luer lock collar 12. This collar includes a needle retainer of one or more laterally flexible lugs. In FIG. 1 lug 14 and lug 16 are shown separated by a longitudinal slot 46. A needle protector 18 encasing a hypodermic needle fits within the Luer lock collar.

This connection is best shown in FIG. 2. Here it is seen that Luer lock collar 12 includes a series of internal threads 20 that engage protruding ears 22 and 24 of a needle hub 26 which in turn is attached to a cannula 28. The needle protector 18 has a rearward end 30 that abuts against the needle hub ears 22, 24. This provides firm bending control of the needle hub by a physician or nurse grasping the needle protector. Preferably the needle protector and needle hub are longitudinally splined together such as at numeral 32 with an interfitting rib and groove structure. There are also a series of sterilization vent ribs on the protector at 34.

The needle hub 26 is wedgingly supported on an externally tapered needle adapter 36. This needle adapter is integrally formed with the syringe barrel and has a circumferential score 38 near its rearward end to weaken the adapter. This score 38 is located within the Luer lock collar 12. In FIG. 2 the needle hub is shown tightly wedged onto a forward portion of the needle adapter while locked thereto by the Luer lock collar. Depending on molding tolerances in manufacturing production, the ears 22 and 24 of the needle hub can be positioned at various longitudinal locations along the Luer lock collar 12 when a tight wedge fit is accomplished on the needle adapter 36.

The sectional view of FIG. 3 shows the interlocking spline system 32 which includes a groove 40 in the protector into which fits a rib 42 of the needle hub. An important feature of our invention is shown in FIG. 4. Here the flexible lugs 13, 14 and 16 are separated by three longitudinal grooves 48, 46, and 50. These three grooves are equally spaced about the circumference of the Luer lock collar. The needle hub preferably has four ears 22, 52, 24, and 54 equally spaced about the circumference of the needle hub, but the hub could have only two ears. Because of the different numbering and spacing of the Luer lock collar slots and needle hub ears, all ears cannot drop into the slots simultaneously. As shown in FIG. 4, needle hub ear 22 has dropped into slot 48 of the Luer lock collar. While in this slot, ear 22 has substantially reduced engagement with the spiral threads 20 of the Luer lock collar. In this position shown in FIG. 4, the other three ears remain spaced from the slots 46 and 50.

In FIG. 5 the needle adapter 36 is shown with its circumferential groove 38. Encircling this needle adapter are the three laterally flexible lugs 13, 14 and 16.

FIG. 6 shows the process for destructing the Luer lock syringe. After a nurse or physician has given a patient an injection with the syringe, the protector 18 is refitted to needle hub 26 until a rear end 30 contacts the needle hub ears. The nurse or physician grasps both the syringe barrel 2 and the needle encasing protector 18 and begins bending the protector. This causes the needle adapter 36 and laterally flexible lug 16 to bend in a common direction. Additional bending in this direction causes the adapter 36 to fracture at score line 38. Thereafter the combined protector, hypodermic needle, and fractured adapter can be removed from the Luer lock collar. The syringe is now very difficult to use for future injections to other patients or by drug addicts.

The above invention works very well when the syringe barrel, segmented Luer lock, and needle adapter are all formed as a one piece homogeneous polypropylene thermoplastic material. The laterally flexible segmented Luer lock also permits longitudinal stripping from the mold. The Luer lock collar can have a thickness, shown at $a$ in FIG. 5, of from 0.010 to 0.025 inch (0.025 to 0.063 cm.) and successful samples have been made with a Luer lock collar thickness of 0.015 inch (0.038 cm.).

This segmented Luer lock collar also permits threads on the Luer lock of a height in the range of 0.015 to 0.030 inch (0.038 to 0.076 cm.) to provide a firm grip on the hub ears. Preferably the threads are approximately 0.020 inch (0.050 cm.) high as shown at b in FIG. 5.

In the foregoing description a specific embodiment of the invention has been used for illustration. It is understood by those skilled in the art that certain modifications can be made to this embodiment without departing from the spirit and scope of the invention.

We claim:

1. A destructible Luer lock syringe comprising: a barrel with a forward end; a needle adapter joined to the barrel's forward end, said adapter and forward end forming a unit having a fracturable section; and a laterally flexible needle retainer connected to the barrel and adapter combination, said needle retainer extending forwardly beyond the unit's fracturable section to a front end of the needle retainer, whereby the adapter and retainer can bend in a common lateral direction for fracturing this fracturable section.

2. A destructible Luer Lock syringe as set forth in claim 1, wherein the laterally flexible retainer is a circumferentially segmented collar with needle engaging means, and each segment of the collar has sufficient lateral stability to firmly hold a needle on the adapter.

3. A destructible Luer lock syringe as set forth in claim 1, wherein the barrel, adapter, and retainer are portions of an integral one-piece thermoplastic unit.

4. A destructible Luer lock syringe as set forth in claim 1, wherein the fracturable section includes a circumferential score line about the adapter.

5. A destructible Luer lock syringe as set forth in claim 1, wherein a hypodermic needle is mounted on the adapter, and the needle engages the retainer, whereby lateral bending of the needle and adapter causes the retainer to laterally flex.

6. A destructible Luer lock syringe as set forth in claim 5, wherein a hollow needle protector fits over the hypodermic needle.

7. A destructible Luer lock syringe as set forth in claim 6, wherein the hypodermic needle has one or more external retaining ears, said ears engaging a rearward end of the protector and extending laterally beyond the protector to contact the retainer, whereby lateral bending forces on the protector can be concentrated adjacent the ears to both fracture the adapter and laterally flex the retainer.

8. A destructible Luer lock syringe as set forth in claim 1, wherein the retainer is an internally threaded collar with one or more longitudinal slots.

9. A destructible Luer lock syringe as set forth in claim 8, wherein a hypodermic needle is fitted on the adapter, and this needle has a plurality of laterally extending ears that engage the collar threads, said ears being of a number and location to prevent all ears simultaneously aligning with the collar slot or slots.

10. A destructible Luer lock syringe as set forth in claim 9, wherein the collar has three slots equally spaced about its circumference, and the hypodermic needle has an even number of ears equally spaced about the needle circumference.

11. A destructible Luer lock syringe comprising a polypropylene barrel with a forward end; and externally tapered needle adapter integrally formed with the barrel's forward end and protruding outwardly therefrom, said adapter having a circumferential score line adjacent the barrel's forward end, a polypropylene retaining collar integrally formed with the barrel's forward end and encircling the needle adapter; said needle adapter having a circumferential score line located within said collar; a hypodermic needle fitted on said adapter; a protector fitting on the needle, with the needle having a plurality of ears that abut a rear end of the protector and extend laterally beyond said protector; internal threads on the collar engaging the needle ears; said collar having a plurality of longitudinal slots permitting one or more segments of the collar to laterally flex during fracture of the adapter, said slots and needle ears having differently spaced circumferential locations so at least one ear is always engaged with the collar threads.

12. A destructible Luer lock syringe as set forth in claim 1, wherein the flexible retainer has a thickness of from 0.010 to 0.025 inch (0.025 to 0.063 cm.).

13. A destructible Luer lock syringe as set forth in claim 1, wherein the flexible retainer has an upstanding thread protruding from an inner surface of the retainer, and this thread has a height in the range of 0.015 to 0.030 inch (0.038 to 0.076 cm).

14. A method of destructing a Luer lock syringe that includes a barrel with a forward end, a needle adapter attached to this forward end, a needle fitted on this adapter, and a needle retainer having a front end and holding the needle on the adapter, comprising the steps of:
   a. bending the needle and adapter in a given direction to place a lateral force on the retainer;
   b. continuing bending said needle and adapter in the same direction causing the needle retainer to flex laterally until a unit formed of the barrel's forward end and the adapter fractures at a location rearward of the needle retainer's front end; and
   c. removing the needle and a fractured portion of the unit from the needle retainer.

15. The method of destroying a Luer lock syringe as set out in claim 14, wherein the method includes substantial flexing of one or more segments of the collar while remaining segments are not substantially flexed in a lateral direction.

16. A luer lock syringe with an internally threaded collar surrounding a needle adapter for coupling to a needle that has a plurality of circumferentially spaced ears for engaging with the collar threads, wherein the improvement in the syringe comprises:
   said collar having a plurality of slots at circumferential locations about the collar which prevent simultaneous collar slot alignment with all ears of said needle, when the syringe is coupled to such needle.

17. A luer lock syringe as set forth in claim 16, wherein a needle with an even number of ears equally spaced about its circumference is coupled to the syringe.

18. A luer lock syringe as set forth in claim 16, wherein the collar has an odd number of slots equally spaced about its circumference.

* * * * *